(12) United States Patent
Rosenberg et al.

(10) Patent No.: US 6,986,884 B2
(45) Date of Patent: Jan. 17, 2006

(54) COMPOSITION AND METHOD FOR TREATING SOFT NAILS

(76) Inventors: E. William Rosenberg, 6055 Sweetbriar Cove, Memphis, TN (US) 38120; Robert B. Skinner, Jr., 347 Riverbluff Pl., Memphis, TN (US) 38103

( * ) Notice: Subject to any disclaimer, the term of this patent is extended or adjusted under 35 U.S.C. 154(b) by 440 days.

(21) Appl. No.: 10/235,881

(22) Filed: Sep. 4, 2002

(65) Prior Publication Data

US 2004/0042982 A1    Mar. 4, 2004

(51) Int. Cl.
*A61K 7/04*    (2006.01)

(52) U.S. Cl. .......................... 424/61; 424/401
(58) Field of Classification Search ................. 424/61, 424/401
See application file for complete search history.

(56) References Cited

U.S. PATENT DOCUMENTS

| | | | |
|---|---|---|---|
| 4,871,533 A | 10/1989 | Lagatore | |
| 4,933,175 A | 6/1990 | Passarelli | |
| 5,478,551 A | 12/1995 | Busch, Jr. | |
| 5,508,027 A | 4/1996 | Witbeck | |
| 5,652,227 A | 7/1997 | Teronen et al. | |
| 5,861,142 A | 1/1999 | Schick | |
| 5,914,099 A | 6/1999 | Yates et al. | |
| 6,124,314 A | 9/2000 | Cameron et al. | |
| 6,200,553 B1 | 3/2001 | Busch, Jr. | |
| 6,248,363 B1 * | 6/2001 | Patel et al. | 424/497 |
| 6,288,120 B1 | 9/2001 | Cameron et al. | |
| 6,352,970 B1 | 3/2002 | Ke et al. | |
| 6,376,502 B1 | 4/2002 | Cameron et al. | |

OTHER PUBLICATIONS

Merck & Co., Inc., FOSAMAX® (Alendronate Sodium Tablets), http://www.druginfonet.com/pi_mfr/pi/merck/fosamax/fosamax.htm, pp. 1-17, Jul. 1997.

* cited by examiner

*Primary Examiner*—Thurman K. Page
*Assistant Examiner*—Sharon Howard
(74) *Attorney, Agent, or Firm*—Pearne & Gordon LLP

(57) ABSTRACT

A composition and method for treating soft nails, particularly soft fingernails, the composition including bisphosphonate, preferably alendronate sodium, in a vehicle effective for topical administration.

23 Claims, No Drawings

COMPOSITION AND METHOD FOR TREATING SOFT NAILS

FIELD OF THE INVENTION

This invention relates to pharmaceutical compositions and more particularly to pharmaceutical compositions and methods for treating soft nails such as fingernails and toenails to make them harder.

DESCRIPTION OF THE RELATED ART

Nail softness is a widespread affliction affecting many humans and animals. Women frequently complain about soft fingernails. Due to the general public's pervasive interest in general well-being and physical appearance, much effort has been expended to find a means of increasing the hardness of otherwise soft nails. Conventionally known nail hardening treatments typically involve calcium and fluoride salts, ammonium hexafluoride phosphate, potassium iodide and other more traditional applications. U.S. Pat. Nos. 5,478,551; 8,200,553; 4,871,533; and 4,933,175, the contents of which are incorporated herein by reference, disclose compositions and methods for the treatment of soft nails.

The methods for treating nail softness disclosed in the above-cited patents have not been sufficiently successful.

Therefore, there is a need for an effective composition and method for treating soft nails and increasing the hardness thereof.

SUMMARY OF THE INVENTION

The present invention provides a pharmaceutical composition for use in treating soft nails, comprising bisphosphonate in a vehicle effective for topical administration to a patient. The present invention also provides a method for treating soft nails of a patient having soft nails tissues, said soft nails tissues comprising said soft nails, said method comprising the step of topically administering to said soft nails tissues of said patient a composition comprising bisphosphonate in a vehicle effective for topical administration to said patient.

DETAILED DESCRIPTION OF THE PREFERRED EMBODIMENTS OF THE INVENTION

As used herein and in the claims, "nails" means fingernails, toenails, claws, talons and hooves; "soft nail tissue" means a soft nail and the tissue surrounding or adjacent the soft nail; "patient" includes humans and animals. As used herein and in the claims, "bisphosphonate", "amino-bisphosphonate", "alendronate", "etidronate", etc. include the pharmaceutically acceptable salts and esters thereof. As used herein, parts are parts by weight and percents are weight percents unless otherwise indicated or apparent. When a preferred range such as 5–25 is given, this means preferably at least 5 and, separately and independently, preferably not more than 25. A nail-hardening agent is an agent for hardening nails.

The inventive composition comprises a nail-hardening agent dissolved, dispersed or carried in a vehicle effective for topical administration to a patient. As used herein and in the claims, a vehicle effective for topical administration to a patient includes creams, ointments, lotions, liniments, gels, solutions, suspensions, and pastes, as well as any other preparation that is pharmaceutically suitable for topical administration on human and/or animal skin and nails. Such vehicles, and their compositions and formulations, are known in the art. The inventive composition, comprising the nail-hardening agent and vehicle, can be provided or dispersed in a conventional manner, including sticks, sprays, aerosols, fluids, gels, creams, etc.

The inventive composition preferably has the formulation and ingredients as described below in Table 1. The nail-hardening agent should be present in a sufficient or effective weight percent effective to produce an effective nail-hardening result in the patient. All values in Table 1 are percentages, by weight. The inventive composition has the following preferred formulation.

TABLE 1

| INGREDIENT | PREFERRED WEIGHT PERCENT | LESS PREFERRED WEIGHT PERCENT | LESS PREFERRED WEIGHT PERCENT | LESS PREFERRED WEIGHT PERCENT | LESS PREFERRED WEIGHT PERCENT |
| --- | --- | --- | --- | --- | --- |
| Nail-Hardening Agent | 0.2 | 0.6 to 0.06 | 2 to 0.02 | 5 to 0.005 | 10 to 0.001 |
| Vehicle | 99.8 | 99.4 to 99.94 | 98 to 99.98 | 95 to 99.995 | 90 to 99.999 |

Less preferably, the composition is 0.0001 to 20 weight percent nail-hardening agent and 80 to 99.9999 weight percent vehicle. The composition comprises a pharmaceutically effective weight percent of nail-hardening agent. The nail-hardening agent is bisphosphonate or a bisphosphonate. More preferably, the nail-hardening agent is an amino-bisphosphonate. More preferably, the nail-hardening agent is alendronate ((4-amino-1-hydroxybutylidene)bis-phosphonate). Even more preferably, the nail-hardening agent is a pharmaceutically acceptable salt of alendronate, such as alendronate sodium ((4-amino-1-hydroxybutylidene) bis-phosphonic acid monosodium salt trihydrate), available under the trademark FOSAMAX from Merck & Co. in Whitehouse Station, N.J.

Other less preferred bisphosphonates may also be used as nail-hardening agents. Such other bisphosphonates include etidronate (1-hydroxyethylidene bis-phosphonate), clodronate (dichloromethylene bis-phosphonate), and pamindronate (3-amino-1-hydroxypropylidene bis-phosphonate). A comprehensive study of known bisphosphonates is provided by Fleisch, H., *Drugs* 42(6):919–944, 1991, the contents of which are incorporated herein by reference. The bisphosphonates useful in carrying out the present invention are, however, not intended to be limited to the above-mentioned compounds.

Preferably, the vehicle is hydrophilic ointment USP or other oil-in-water cream. Alternatively, the vehicle can be an emulsion having water with enough oil to make it spread, such as a vanishing cream base, or other oil and water or water and oil emulsion or emulsion base. Other vehicles known in the art may be used, preferably those suitable for carrying water-soluble components. A less preferred vehicle is polyethylene glycol.

As part of the vehicle, emollients, humectants, and other customary additives can be included in conventional amounts. Other preferred vehicles for the inventive composition are described as follows. For example, the vehicle can be an oil system, such as fat or oil or synthetic fat such as petrolatum. Alternatively, the vehicle can be (1) a lotion, such as water and fat or oil with an emulsifier and with or without ethanol; (2) a cream or cream base, which is generally the same as a lotion but with less water and a higher viscosity and customarily a higher concentration of the active ingredients; (3) an ointment, which is generally the same as a cream but without the water; it is nearly 100% oil or fat; (4) a gel, which is normally water only which optionally can have a little ethanol but with no or substantially no fat or oil; a thickening agent is added to provide gel viscosity; (5) a foam, which is generally an emulsified type of cream; or (6) a solution or suspension of water or ethanol or a mixture thereof, without fat or oil, and with an emulsifier as needed. Alternatively, the composition can be provided as or in a liniment, a paste, a stick, an aerosol, or other suitable form.

The vehicle of the composition comprises all ingredients and additives (including optional and/or customary additives as described above) present in the composition other than the nail-hardening agent. Therefore, it is understood that the weight percentage of the vehicle of the composition, e.g., as listed in Table 1, will vary depending only on the weight percentage of the nail-hardening agent in the composition.

The ingredients of the composition or formulation are blended and combined in a conventional manner to provide the inventive composition as described above.

The inventive composition is applied in a conventional manner to a human's or animal's nail tissue such as fingernails, toenails, claws, talons, hooves, etc. It is rubbed onto the nail and onto and into the flesh and tissues surrounding the nail, particularly where the nail emerges from the flesh. Preferably, the composition is applied to the nail tissue according to a periodic regime (e.g. daily, weekly, etc.) for a period of time sufficient to harden or increase the hardness of the previously soft nails. For example, the inventive composition is preferably applied about or at least once daily, twice daily, three times daily, four times daily, once weekly, twice weekly, three times weekly, or four times weekly, less preferably some other suitable interval. The treatment should be applied when the nails are soft or not sufficiently hard for the desires or needs of the patient and should be continued until the desired result is achieved.

The following Examples 1–3 further illustrate various aspects of the invention.

EXAMPLE 1

A 73 year old Caucasian woman has had soft fingernails for as long as she can remember. She did not have osteoporosis and was in good health. Three months after twice daily applications of a 0.2% alendronate ointment (hydrophilic ointment USP vehicle) to the skin around her fingernail folds, the nails were visibly harder. Six months later, they were very hard and have remained so for one year with continued twice daily applications of the alendronate ointment.

EXAMPLE 2

A 59 year old man developed very soft, troublesome fingernails after beginning to take acitretin 25mg/day as a treatment for his psoriasis. He began twice daily applications of 0.2% alendronate ointment (polyethylene glycol vehicle) to the skin around his fingernail folds while continuing to take acitretin. After three months of using the alendronate ointment, his nails were no longer too soft or troublesome.

EXAMPLE 3

A 76 year old retired physician and his 60 year old wife both were troubled by soft fingernails. Both were in otherwise good health and did not have osteoporosis. Twice daily applications of 0.2% alendronate ointment (polyethylene glycol vehicle) had improved both of their fingernails after four months of use.

The results of Examples 1–3 were surprising and unexpected.

Although the preferred embodiments have been described, it is understood that various modifications may be resorted to without departing from the scope of the invention as disclosed and claimed herein.

What is claimed is:

1. A pharmaceutical composition for use in treating soft nails of a patient, said composition comprising bisphosphonate in a vehicle, said composition being in a form effective for topical administration to soft nails tissues of said patient.

2. The composition of claim 1, wherein said composition is 0.0001 to 20 weight percent bisphosphonate.

3. The composition of claim 1, wherein said composition is 5 to 0.005 weight percent bisphosphonate.

4. The composition of claim 1, wherein said vehicle comprises water and oil.

5. The composition of claim 1, wherein said bisphosphonate is an amino-bisphosphonate.

6. The composition of claim 1, wherein said bisphosphonate is alendronate.

7. The composition of claim 1, wherein said bisphosphonate is a salt of alendronate.

8. The composition of claim 1, wherein said bisphosphonate is alendronate sodium.

9. The composition of claim 1, wherein said vehicle is hydrophilic ointment USP.

10. The composition of claim 1, wherein said composition is 2 to 0.02 weight percent bisphosphonate.

11. A method for treating soft nails of a patient having soft nails tissues, said soft nails tissues comprising said soft nails, said method comprising the step of topically administering to said soft nails tissues of said patient a composition comprising bisphosphonate in a vehicle, said composition being in a form effective for topical administration to said soft nails tissues of said patient.

12. The method of claim 11, wherein said patient is a human.

13. The method of claim 11, wherein said composition is 0.0001 to 20 weight percent bisphosphonate.

14. The method of claim 11, wherein said composition is 5 to 0.005 weight percent bisphosphonate.

15. The method of claim 11, wherein said vehicle comprises water and oil.

16. The method of claim 11, wherein said bisphosphonate is an amino-bisphosphonate.

17. The method of claim 11, wherein said bisphosphonate is alendronate.

18. The method of claim 11, wherein said bisphosphonate is a salt of alendronate.

19. The method of claim 11, wherein said bisphosphonate is alendronate sodium.

20. The method of claim 11, wherein said vehicle is hydrophilic ointment USP.

21. The method of claim 11, wherein said composition is 2 to 0.02 weight percent bisphosphonate.

22. The composition of claim 1, wherein said composition is a cream, ointment, lotion or liniment.

23. The method of claim 11, said method including topically administering said composition to said soft nails tissues according to a periodic regime for a period of time effective to increase the hardness of said soft nails.

* * * * *